(12) United States Patent  
Hill et al.

(10) Patent No.: US 7,710,564 B1
(45) Date of Patent: May 4, 2010

(54) POLARIZED BROADBAND WAFER INSPECTION

(75) Inventors: Peter Hill, Palo Alto, CA (US); Robert Danen, San Jose, CA (US); Charles N. Wang, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 237 days.

(21) Appl. No.: 12/109,831

(22) Filed: Apr. 25, 2008

Related U.S. Application Data

(60) Provisional application No. 60/969,661, filed on Sep. 3, 2007.

(51) Int. Cl.
*G01J 4/00* (2006.01)
(52) U.S. Cl. ...................................... 356/369
(58) Field of Classification Search ................... 356/369
See application file for complete search history.

(56) References Cited

U.S. PATENT DOCUMENTS 7,525,712 B2 * 4/2009 Wen et al. ................... 359/252

* cited by examiner

*Primary Examiner*—Roy Punnoose
(74) *Attorney, Agent, or Firm*—Luedeka, Neely & Graham, P.C.

(57) ABSTRACT

In one embodiment, a surface inspection system comprises a radiation directing assembly to target radiation onto a surface of an object, the radiation directing assembly comprising a radiation source that emits a broadband radiation beam, a polarization control assembly comprising at least one of a linear polarizer and an apochromatic retarder, an aperture control mechanism, and a beam splitter, a radiation collection assembly to collect radiation reflected from the surface of the object, the radiation collection assembly comprising, a polarization control assembly comprising at least one of a linear polarizer and an apochromatic retarder, an aperture control mechanism, and at least one radiation sensing device.

19 Claims, 9 Drawing Sheets

S-Type Apertures

Polarization Vector Orientation

Aperture

P-Type Apertures

Polarization Vector Orientation

Aperture

Cross Polarization Aperture (X/Y)

Cross Polarization Aperture (S/P)

Cross Polarization Aperture
(RH/LH)

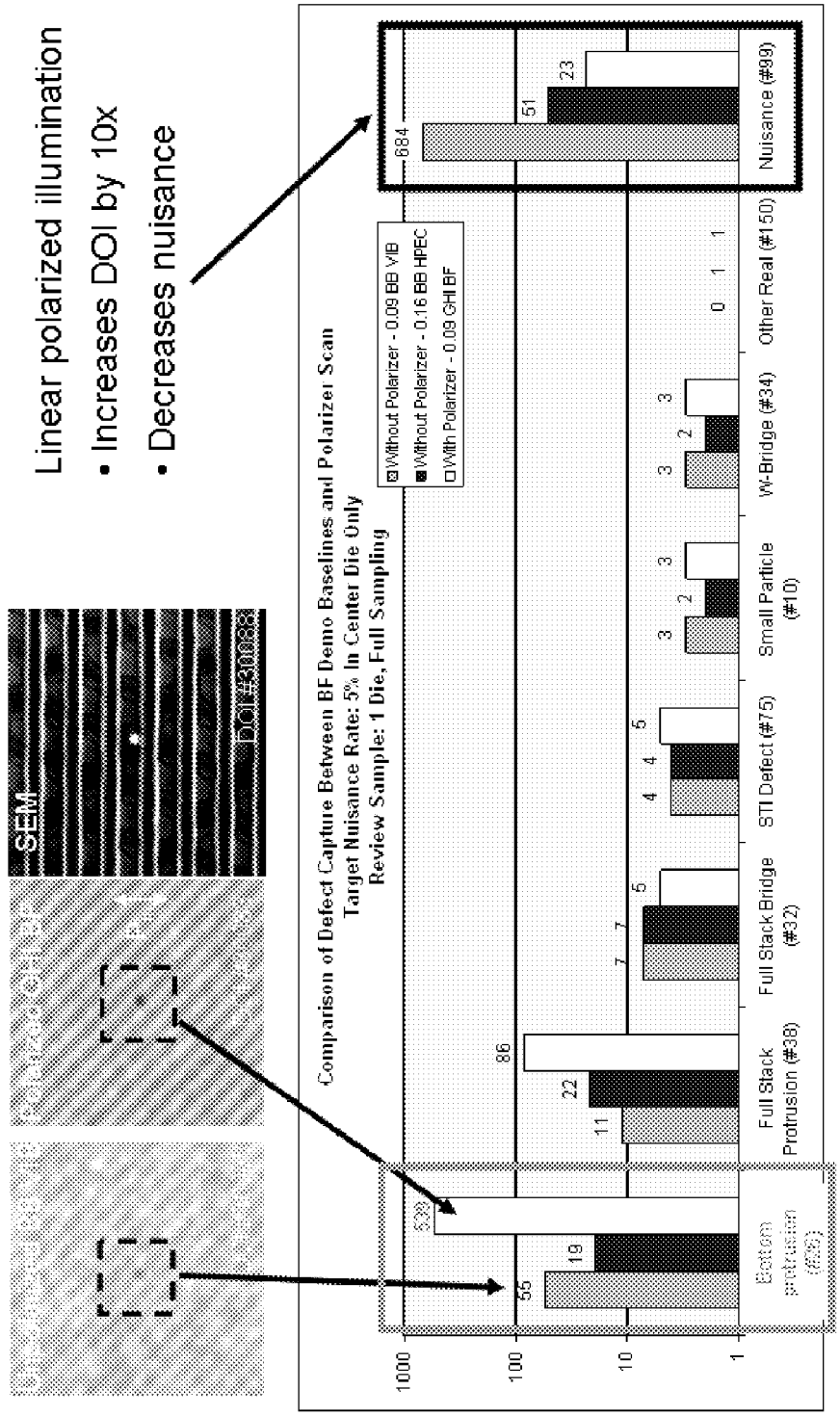
Figure 9: Polarization control can improve sensitivity 70nm DRAM gate etch bottom protrusions

Figure 10: Camera S/N
Green > 1.3, 1.3 > yellow < 1.0, red < 1.0
DOI
| CONFIG | POL ILL | 29321 | 29585 | 29661 | 29837 | 30088 | 30756 | 30935 | 31146 | 31327 | 32030 | 32048 | 32060 | 32121 | 32201 |
|---|---|---|---|---|---|---|---|---|---|---|---|---|---|---|---|
| BB VIB | none | 1.14 | 1.01 | 0.97 | 0.91 | 0.82 | 1.11 | 0.82 | 1.04 | 1.33 | 0.88 | 1.01 | 1.19 | 0.93 | 1.17 |
| BB VIB | 0 | 0.76 | 0.78 | 0.84 | 1.03 | 0.73 | 0.90 | 1.07 | 1.27 | 1.23 | 0.86 | 0.76 | 0.96 | 0.81 | 0.93 |
| BB VIB | 90 | 1.62 | 1.34 | 1.23 | 1.12 | 1.33 | 1.50 | 1.13 | 1.29 | 1.62 | 1.47 | 1.28 | 1.44 | 0.97 | 1.26 |
| GHI BF | none | 1.00 | 1.04 | 0.92 | 1.03 | 0.88 | 1.02 | 0.99 | 1.15 | 1.72 | 0.95 | 1.28 | 0.91 | 0.95 | 1.24 |
| GHI BF | 0 | 0.84 | 0.79 | 0.71 | 0.74 | 0.83 | 0.86 | 0.89 | 1.00 | 0.90 | 0.73 | 0.85 | 0.79 | 0.80 | 0.84 |
| GHI BF | 90 | 2.58 | 1.89 | 1.96 | 1.85 | 2.09 | 2.54 | 2.03 | 2.55 | 2.65 | 2.01 | 2.82 | 2.16 | 1.88 | 2.10 |
NUISANCE
| CONFIG | POL ILL | 32168 | 32175 | 32186 | 32196 | 32266 | 32343 | 33588 | 33589 | 33599 | 33613 | 33616 | 33617 | 33671 | 34009 |
|---|---|---|---|---|---|---|---|---|---|---|---|---|---|---|---|
| BB VIB | none | 0.73 | 0.73 | 0.77 | 0.91 | 0.73 | 0.91 | 0.80 | 0.74 | 0.76 | 0.73 | 0.87 | 0.71 | 0.86 | 0.94 |
| BB VIB | 0 | 0.83 | 0.77 | 0.81 | 0.80 | 0.75 | 0.69 | 0.74 | 0.83 | 0.76 | 0.77 | 0.76 | 0.99 | 0.86 | 0.76 |
| BB VIB | 90 | 0.61 | 0.73 | 0.87 | 0.95 | 0.67 | 0.92 | 0.90 | 0.69 | 0.82 | 0.74 | 0.88 | 0.68 | 0.77 | 0.81 |
| GHI BF | none | 0.82 | 0.85 | 0.72 | 0.80 | 0.82 | 0.93 | 0.75 | 0.74 | 0.84 | 0.82 | 0.79 | 1.05 | 0.71 | 0.77 |
| GHI BF | 0 | 0.87 | 0.87 | 0.73 | 0.82 | 0.88 | 1.02 | 0.76 | 0.96 | 0.71 | 0.88 | 0.80 | 0.98 | 0.71 | 0.72 |
| GHI BF | 90 | 0.70 | 0.68 | 0.74 | 0.77 | 0.71 | 0.83 | 0.71 | 0.88 | 0.76 | 0.80 | 1.00 | 0.72 | 0.76 | 0.73 |
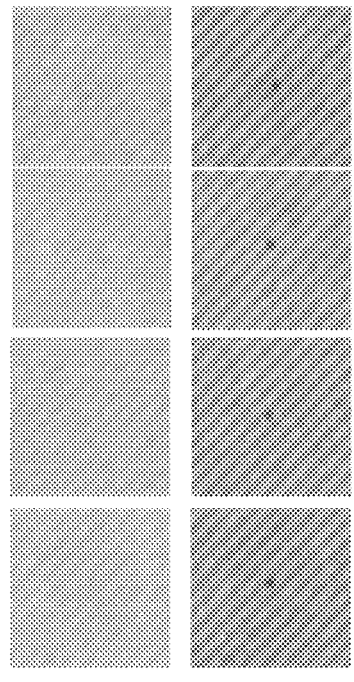
GHI BF Unpol
GHI BF P90
Noise = 4.5 * sigma
Polarization control improves DOI S/N for range of wavelengths and modes.

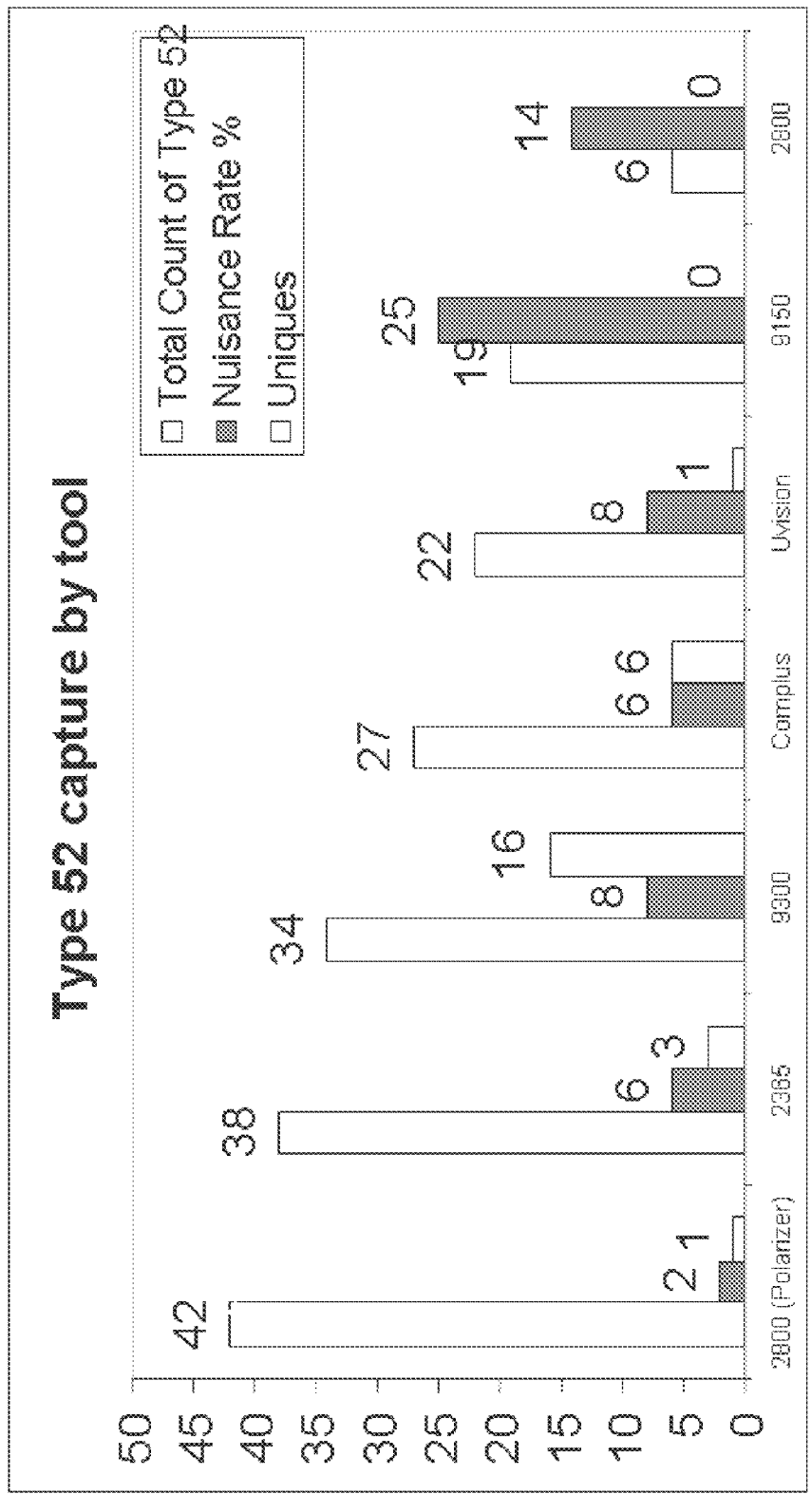

Figure 12: Polarized Inspection shows cap rate improvement ESD Layer

| Caprate | Defect Count | Cum Total | Avg Caprate |
|---|---|---|---|
| 100 | 67 | 6700 | |
| 90 | 17 | 1530 | |
| 80 | 14 | 1120 | |
| 70 | 18 | 1260 | |
| 60 | 13 | 780 | |
| 50 | 15 | 750 | |
| 40 | 17 | 680 | |
| 30 | 23 | 690 | |
| 20 | 20 | 400 | |
| 10 | 46 | 460 | |
| Total | 250 | 14370 | 57.48 |

| Caprate | Defect Count | Cum Total | Avg Caprate |
|---|---|---|---|
| 100 | 148 | 14800 | |
| 90 | 15 | 1350 | |
| 80 | 15 | 1200 | |
| 70 | 9 | 630 | |
| 60 | 7 | 420 | |
| 50 | 11 | 550 | |
| 40 | 8 | 320 | |
| 30 | 10 | 300 | |
| 20 | 13 | 260 | |
| 10 | 6 | 60 | |
| Total | 242 | 19890 | 82.19008264 |

POLARIZED BROADBAND WAFER INSPECTION

RELATED APPLICATIONS

This application claims the benefit of priority under 35 U.S.C. §119(e) to U.S. Provisional Application No. 60/969,661, filed Sep. 3, 2007.

BACKGROUND

The subject matter described herein relates to surface inspection techniques, and more particularly to systems and methods for wafer inspection that utilize polarized broadband radiation.

Semiconductor materials may be inspected for defects such as, e.g., surface imperfections, particles, irregularities in the thickness of thin film coatings, and the like, which may hamper the performance of the semiconductor material. Some existing inspection systems direct a beam of radiation on the surface of the semiconductor material, then collect and analyze light reflected and/or scattered from the surface to quantify characteristics of the surface. Additional inspection techniques are desirable.

BRIEF DESCRIPTION OF THE DRAWINGS

FIG. 9 is a graph illustrating defect capture rates using polarized radiation, according to embodiments.

FIG. 10 is a graph illustrating signal to noise ratios using polarized radiation, according to embodiments.

FIG. 11 is a graph illustrating defect captures using polarized radiation, according to embodiments.

FIG. 12 is graphs illustrating cap improvements in inspection systems, according to embodiments.

DETAILED DESCRIPTION

Described herein are exemplary systems and methods for polarized broadband wafer inspection. Throughout this document, terms like light, optical, optics, rays and beams with reference to electromagnetic radiation may be used with no implication that the radiation is or is not in the visible portion of the spectrum. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

In some embodiments, the systems and methods described herein provide polarization control of a broadband ultra-violet, including deep ultra-violet, flexible brightfield and darkfield imaging system for wafer inspection with high sensitivity and high throughput. Examples of such systems and methods are described in U.S. Pat. No. 7,304,310 to Schortt, et al., entitled Methods and Systems for Inspecting a Specimin Using Light Scattered in Different Wavelength Ranges, U.S. Pat. No. 7,259,844 to Fairley, et al. entitled High Throughput Darkfield/Brightfield Wafer Inspection Systems Using Advanced Optical Techniques, and U.S. Pat. No. 7,002,677 to Bevis, et al., entitled Darkfield Inspection System Having a Programmable Light Selection Array, the disclosures of which are incorporated herein by reference in their entireties.

In some embodiments, an inspection system utilizes a wire-grid polarizer with fine pitch, relative to the wavelength of the radiation used by the inspection system. For example, in some embodiments the wire grid polarizer may have a pitch (i.e., distance between wires) that is less than half the shortest wavelength of radiation used by the inspection system to inspect surfaces. FIG. 1B is a schematic illustration of a wire grid polarizer which may be used in an inspection system, according to embodiments. In such embodiments, the wire grids with fine pitch 102 may be manufactured on a fused substrate 104. Wire-grid polarizers with fine pitch polarize light with sufficient transmission and extinction over a broad range of wavelengths to be useful in a broadband wafer inspection system. In addition, wire-grid polarizers are robust under DUV exposure and can be fabricated to satisfy requirements of high sensitivity optical systems (e.g., thin substrate to minimize aberrations). Further, some methods to fabricate grid polarizers lend to fabrication of polarizers with a transmitted polarization vector orientation that varies across the part, which could be useful for wafer inspection systems that incorporate large numerical aperture (NA) for either illumination or imaging.

Figure 1A:
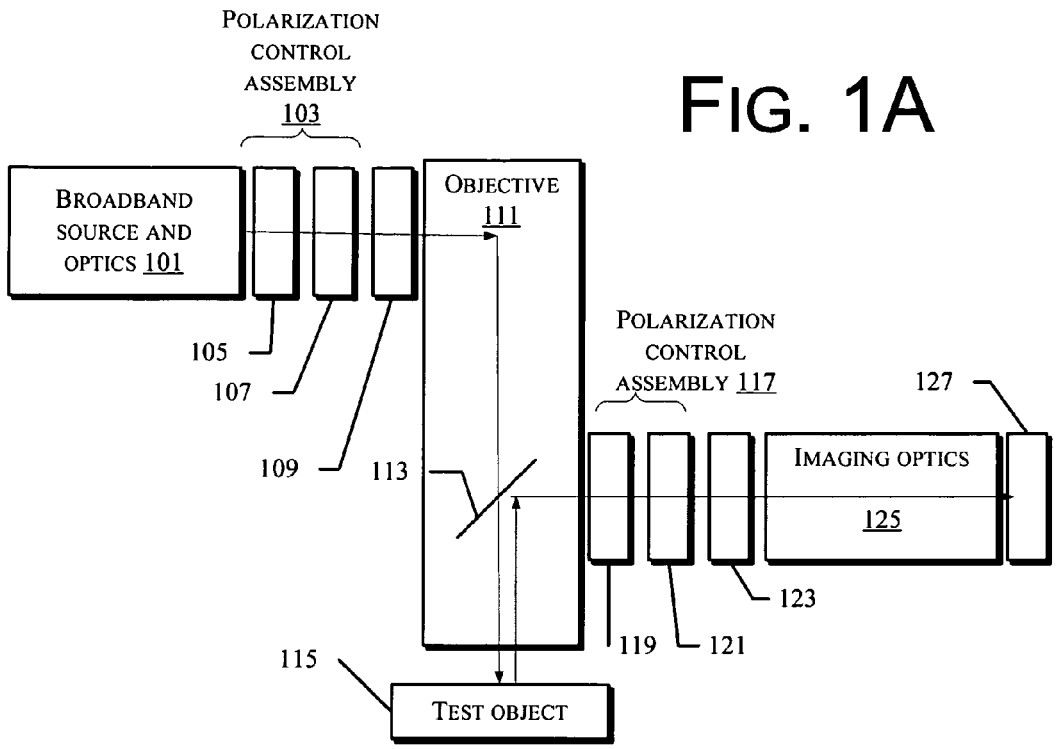
FIG. 1A is a schematic illustration of an inspection system, according to embodiments.
Figure 1B:
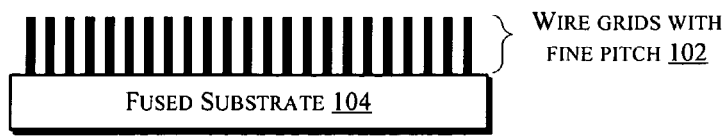
FIG. 1B is a schematic illustration of a wire grid polarizer which may be used in an inspection system, according to embodiments.

FIG. 1A shows a diagram of a wafer inspection system with polarization control. Light emitted from a broadband source 101 is illuminated onto a test object 115 and imaged onto a time delay integration (TDI) detector 127. The polarization of the light source is controlled in both illumination and imaging paths by manipulating a linear polarizer 105, 119 (e.g., wire grid) and apochromatic retarder 107, 121 pair. In some embodiments, different apertures 109, 123 may be placed in the illumination pupils 101 and imaging pupils 125 to dampen the polarization aberrations caused by the specimen and the inspection system to enhance the purity of the desired polarization both at the specimen and the TDI detector 127.

The broadband wafer inspection system controls a polarization vector of the source and the polarization vector near the imaging plane to enhance the system's sensitivity to specific objects located on the inspected specimen. Polarization control is made possible through the appropriate orientation of a linear polarizer which operates over a broad range of wavelengths. The ellipticity of the polarization vector may be modified with an apochromatic retarder 107, 121. Sensitivity can be further enhanced by masking the polarized beam with an appropriate aperture set 109, 123 (see FIGS. 2, 3, 4, 5, and 6). The apparatus allows for polarization and aperture control in both illumination and imaging paths. The physical location of the linear polarizer 105, 119 and apochromatic retarder 107, 121 is flexible: They can be located either close to pupil plane, close to field plane or any other favorable location to enhance the object of interest which may have variable amplitude and phase properties.

With the correct polarization and aperture configuration 109, 123, a larger concentration of the electric field may be localized at a specific layer of the specimen, making the inspection system more sensitive to targeted objects of interest while suppressing noise from previous or overlaying layer (see FIGS. 9, 10, 11 and 12). The advantage of the fine pitch wire-grid polarizer is its performance across a broad spectrum to DUV wavelengths.

Multiple fabrication methods may be used to construct wire-grid polarizers as well as other optical components capable of polarizing deep ultraviolet (DUV) light for inspection systems and is not meant to limit the scope of the invention. In some embodiments, fine pitch wire grid polarizers may be produced using 266 nm, 193 and other DUV interference lithography systems, immersion lithography, dual patterning lithography, combination of interference, immersion or dual patterning lithography, EUV lithography, e-Beam writing and nanoimprint technologies.

Some of these methods permit fabrication of polarizers with a transmitted polarization vector orientation that varies across the polarizer. This could be used to generate or analyze linear polarization vectors that vary as a function of incident angle or reflected/scattered angle at the wafer specimen.

Dielectric fine-pitch grids and diffraction gratings are capable of polarizing light, but they generally polarize for a narrow range of wavelengths. For broadband applications, use of several grids or gratings designed for varying wavelengths stacked in series may be used to polarize broadband DUV radiation.

A multi-layer coating on a plane parallel plate is capable of obtaining both high extinction and high transmission, however, such a design is limited to both narrowband and narrow angle applications. A combination in series of any narrow band polarizers may be used to produce a broadband polarizer.

A series of plane parallel plates oriented at Brewster's angle is able to polarize a broadband source, however, the design is limited to a narrow scope of angles. In addition, the large amount of glass needed for the design leads to increased wavefront distortion. Further, the large number of air to glass interfaces would increase the number of ghost reflections in the system.

Another approach to polarizing a broadband ultraviolet source is to use a polarizing prism. It is difficult to manufacture a large one, however, due to the difficulty in obtaining a large crystal with adequate homogeneity. In addition, polarizing prisms have a much smaller acceptance angle than the polarizing element described. Last, the large amount of glass required for the part leads to a larger amount wavefront distortion.

Various processing techniques may be used produce these polarizers: 266 nm, 193 and other DUV interference lithography systems, immersion lithography, dual patterning lithography, combination of interference, immersion or dual patterning lithography, EUV lithography, e-Beam writing and nanoimprint technologies.

In some embodiments, the tailored polarizers having a transmitted polarization vector orientation that varies across the part may be used. For example, in some embodiments multiple wire-grid patterns may be printed, oriented at different but certain directions across polarizer part substrate. For example, if the wire grids are oriented along the radial direction of the polarizer part, P-polarized light could be utilized for wafer inspection. Contrarily, if the wire grids are oriented along a circumference, S-polarized light could be utilized for wafer inspection.

Figure 2:
FIGS. 2-6 are schematic illustrations of polarization apertures which may be used in an inspection system, according to embodiments.
Figure 2:
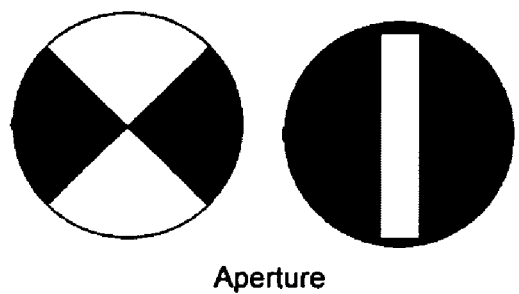
Figure 3:
Figure 3:
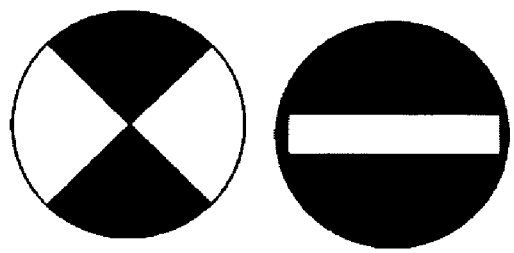
Figure 4:
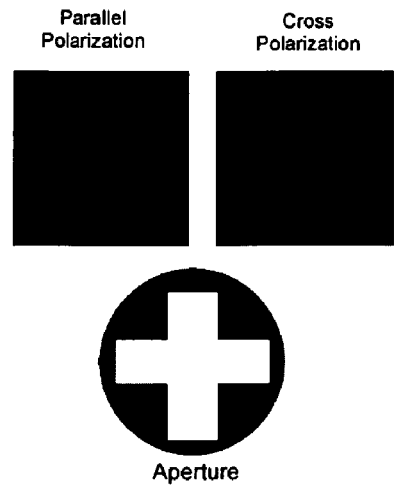
Figure 5:
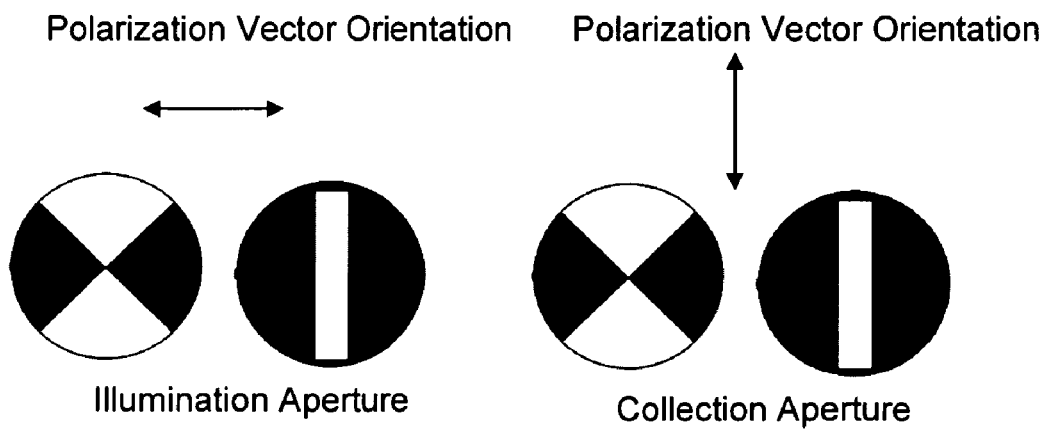
Figure 6:
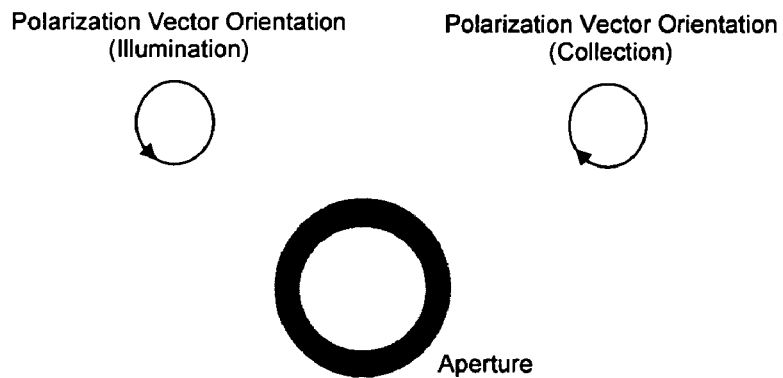
Figure 7:
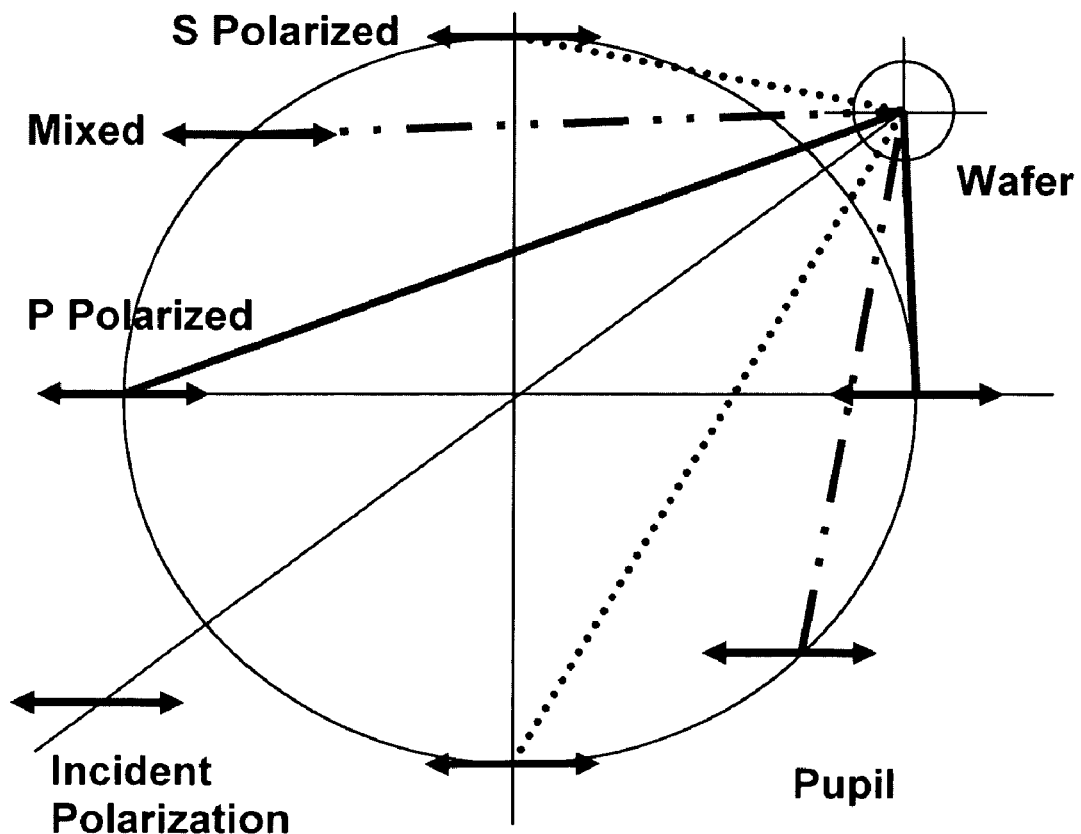
FIG. 7 is a schematic illustration of polarization orientations of radiation incident on the surface of a wafer, according to embodiments.

FIG. 7 shows how X and Y polarization at the illumination pupil are found to have different S and P projections at the wafer which vary as a function of the pupil position. Aside from having the ability to target specific layers on an inspected specimen, FIGS. 2 and 3 show apertures that have the benefit of sharpening the image by removing birefringent effects present in the system.

By placing the illumination and collection polarizers in orthogonal orientations, the apparatus can be used as a broadband, cross-polarized imaging system. A special aperture may be inserted to improve the extinction ratio of this mode by blocking the leakage created in the four quadrants of a high NA cross polarization imaging system (see FIGS. 4 and 6).

In addition, a quarter wave plate may be inserted into the illumination or collection path to alter the generated/analyzed linear state to a circular state. By rotating the quarter wave plate, the ellipticity of the polarization may be changed to vary the penetration depth of the incident electric field.

Figure 8:
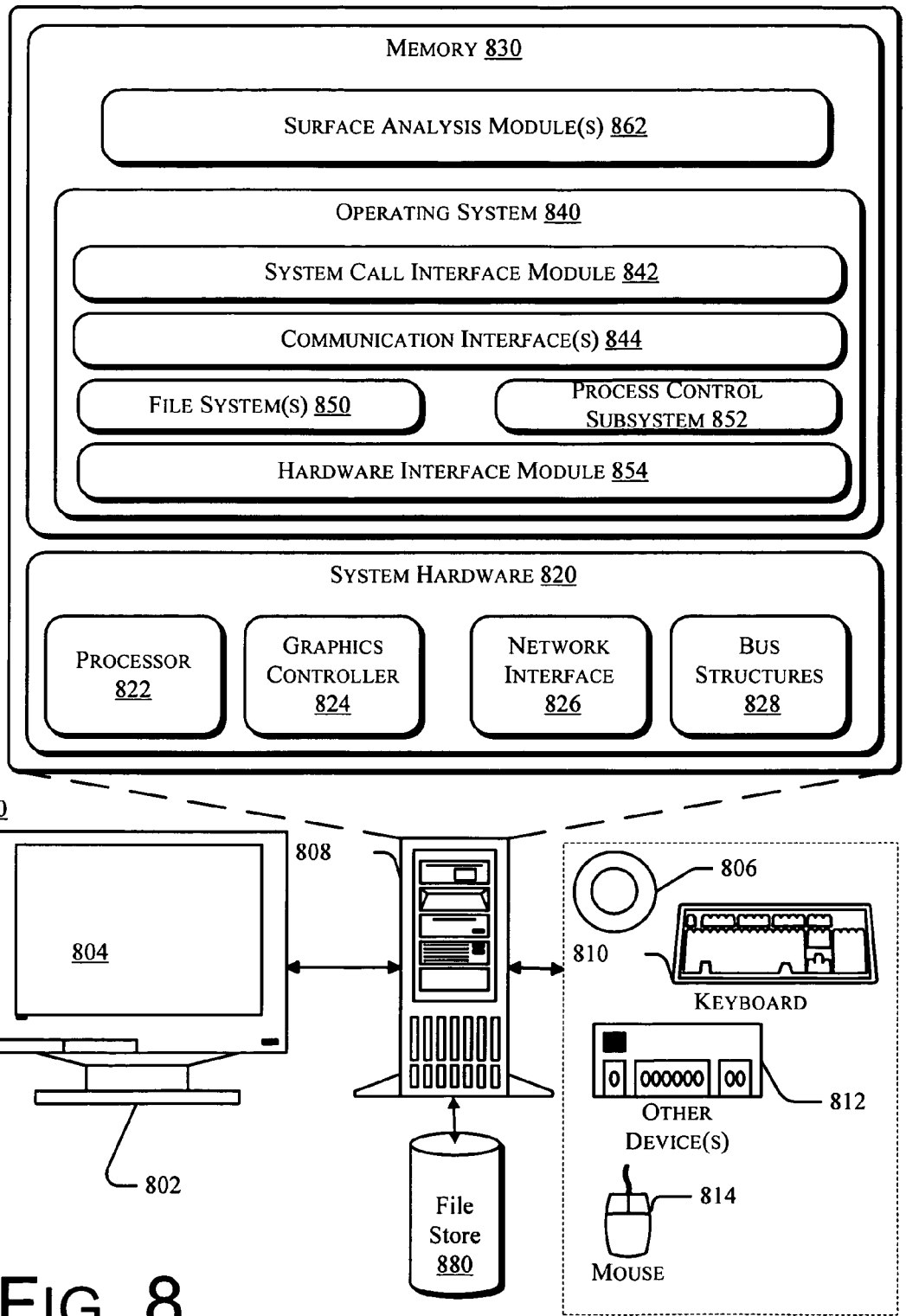
FIG. 8 is a schematic illustration of a computing system which may implement polarization inspection systems, according to embodiments.

FIG. 8 is a schematic illustration of one embodiment of a computing system which may be used to process data received from the imaging optics 125 of FIG. 1A. The computer system 800 includes a computer 808 and one or more accompanying input/output devices 806 including a display 802 having a screen 804, a keyboard 810, other I/O device(s) 812, and a mouse 814. The other device(s) 812 can include a touch screen, a voice-activated input device, a track ball, and any other device that allows the system 800 to receive input from a developer and/or a user. The computer 808 includes system hardware 820 and random access memory and/or read-only memory 830. A file store 880 is communicatively connected to computer 808. File store 880 may be internal such as, e.g., one or more hard drives, or external such as, e.g., one or more external hard drives, network attached storage, or a separate storage network.

Memory 830 includes an operating system 840 for managing operations of computer 808. In one embodiment, operating system 840 includes a hardware interface module 854 that provides an interface to system hardware 820. In addition, operating system 840 includes one or more file systems 850 that manage files used in the operation of computer 808 and a process control subsystem 852 that manages processes executing on computer 808. Operating system 840 further includes a system call interface module 842 that provides an interface between the operating system 840 and one or more application modules 862.

In operation, one or more application modules and/or libraries executing on computer 808 make calls to the system call interface module 842 to execute one or more commands on the computer's processor. The system call interface module 842 invokes the services of the file system(s) 850 to manage the files required by the command(s) and the process control subsystem 852 to manage the process required by the command(s). The file system(s) 850 and the process control subsystem 852, in turn, invoke the services of the hardware interface module 854 to interface with the system hardware 820.

The particular embodiment of operating system 840 is not critical to the subject matter described herein. Operating system 840 may be embodied as a UNIX operating system or any derivative thereof (e.g., Linux, Solaris, etc.) or as a Windows® brand operating system.

In some embodiments, computer system 800 includes one or more modules to implement a surface inspection system. In the embodiment depicted in FIG. 8, computer system 800 includes a surface analysis module 862 which implements the system described with reference to FIG. 1A.

Using broadband, linear polarized light for inspection has the benefit of targeting specific layers of a specimen while controlling defect contrast with wavelength. Such a configuration has the benefit of maximizing sensitivity to the area of interest while minimizing noise. By way of example and not limitation, consider FIGS. 9, 10 and 11 which show that orienting the polarization vector such that it is perpendicular to a line space array will penetrate the electric field deeper into the specimen, increasing the capture rate of objects of interest embedded within the dense structure. Conversely, orienting the polarization parallel to the line space array will concentrate the electric field at the surface of structure, making the inspection system sensitive to the objects such as particles on the surface of the wafer specimen. These examples make use of a single polarizer in either the illumination or imaging paths of the inspection system.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A surface inspection system, comprising:
   a radiation directing assembly to target radiation onto a surface of an object, the radiation directing assembly comprising:
      a polarization control assembly comprising at least one of a linear polarizer and an apochromatic retarder;
      an aperture control mechanism; and
      a beam splitter;
   a radiation collection assembly to collect radiation reflected from the surface of the object, the radiation collection assembly comprising:
      a polarization control assembly comprising at least one of a linear polarizer and an apochromatic retarder;
      an aperture control mechanism; and
      at least one radiation sensing device.

2. The radiation directing assembly of claim 1, further comprising a radiation source that emits a broadband radiation beam.

3. The surface inspection system of claim 1, wherein the linear polarizer comprises a wire grid polarizer.

4. The wire grid polarizer of claim 3, wherein the pitch of the wire grid polarizer is shorter than the shortest inspection wavelength for an object to be tested divided by two.

5. The wire grid polarizer of claim 3, wherein the wire grid polarizer is fabricated with transmitted polarization vector orientations that vary by a known amount across the polarizer.

6. The surface inspection system of claim 1, wherein the linear polarizer comprises a series of wire grid polarizer designed for varying wavelengths.

7. The surface inspection system of claim 1, wherein the polarization control assembly is placed at a predetermined location along the radiation directing assembly wherein the predetermined location is selected to enhance measurement of an object of interest.

8. The surface inspection system of claim 1, wherein the polarization control assembly is placed at a predetermined location along the radiation collection assembly wherein the predetermined location is selected to enhance measurement of an object of interest.

9. The surface inspection system of claim 1, further comprising S-Type apertures used in at least one of the aperture control mechanisms so as to dampen polarization aberrations and enhance measurement sensitivity.

10. The surface inspection system of claim 1, further comprising P-Type apertures used in at least one of the aperture control mechanisms so as to dampen polarization aberrations and enhance measurement sensitivity.

11. The surface inspection system of claim 1, further comprising XY cross polarization apertures used in at least one of the aperture control mechanisms so as to dampen polarization aberrations and enhance measurement sensitivity.

12. The surface inspection system of claim 1, further comprising SP cross polarization apertures used in at least one of the aperture control mechanisms so as to dampen polarization aberrations and enhance measurement sensitivity.

13. The surface inspection system of claim 1, further comprising RH/LH cross polarization apertures used in at least one of the aperture control mechanisms so as to dampen polarization aberrations and enhance measurement sensitivity.

14. A polarization control assembly comprising:
    at least one of a linear polarizer; and
    an apochromatic retarder.

15. The polarization control assembly of claim 14, wherein the linear polarizer comprises a wire grid polarizer.

16. The wire grid polarizer of claim 15, wherein the pitch of the wire grid polarizer is shorter than the shortest inspection wavelength for an object to be tested divided by two.

17. The wire grid polarizer of claim 15, wherein the wire grid polarizer is fabricated with transmitted polarization vector orientations that vary by a known amount across the polarizer.

18. The polarization control assembly of claim 14, wherein the apochromatic retarder modifies the ellipticity of the polarization vector.

19. The polarization control assembly of claim 14, wherein the linear polarizer comprises a series of wire grid polarizer designed for varying wavelengths.

* * * * *